(12) United States Patent
Li et al.

(10) Patent No.: US 12,383,229 B2
(45) Date of Patent: Aug. 12, 2025

(54) CAPACITIVE ULTRASONIC TRANSDUCER DEVICE, MANUFACTURING METHOD THEREOF AND TRANSDUCER ARRAY

(71) Applicant: NATIONAL TSING HUA UNIVERSITY, Hsinchu (TW)

(72) Inventors: Sheng-Shian Li, Taoyuan (TW); Hung-Yu Chen, Taichung (TW); Ming-Huang Li, Pingtung County (TW); Po-I Shih, Taoyuan (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 271 days.

(21) Appl. No.: 18/067,721

(22) Filed: Dec. 18, 2022

(65) Prior Publication Data

US 2024/0099695 A1    Mar. 28, 2024

(30) Foreign Application Priority Data

Sep. 28, 2022 (TW) .................................. 111136868

(51) Int. Cl.
*A61B 8/00* (2006.01)
(52) U.S. Cl.
CPC .......... *A61B 8/4488* (2013.01); *A61B 8/4494* (2013.01)
(58) Field of Classification Search
None
See application file for complete search history.

(56) References Cited

U.S. PATENT DOCUMENTS

| 9,029,178 B2 * | 5/2015 | Larrey ................. B06B 1/0292 |
|  |  | 438/758 |
| 10,196,261 B2 * | 2/2019 | Rothberg ............ B81C 1/00182 |
| 2009/0250729 A1 | 10/2009 | Lemmerhirt et al. |

(Continued)

FOREIGN PATENT DOCUMENTS

TW           201834025 A       9/2018

OTHER PUBLICATIONS

Chen, Hung-Yu, et al. "Platform development for CMOS-MEMS multi-gap capacitive transducers." Journal of Microelectromechanical Systems 32.5 (2023): 461-473. (Year: 2023).*

(Continued)

*Primary Examiner* — Isam A Alsomiri
*Assistant Examiner* — Jonathan D Armstrong
(74) *Attorney, Agent, or Firm* — CKC & Partners Co., LLC

(57) ABSTRACT

A capacitive ultrasonic transducer device includes a substrate, a first capacitive structure, a second capacitive structure, a first film structure and a second film structure. The first capacitive structure is disposed on the substrate, and includes a first electrode and a second electrode. A first gap and a dielectric layer are located between the first electrode and the second electrode. The second capacitive structure is disposed on the substrate, and includes a third electrode and a fourth electrode. A second gap is located between the third electrode and the fourth electrode. The first film structure is configured to seal the first gap. The second film structure is connected to the third electrode and the fourth electrode, and configured to seal the second gap. A first width between the first electrode and the second electrode is different from a second width of the second gap.

8 Claims, 13 Drawing Sheets

(56) References Cited

U.S. PATENT DOCUMENTS

| | | | |
|---|---|---|---|
| 2012/0058587 A1 | 3/2012 | Chang et al. | |
| 2013/0069480 A1* | 3/2013 | Akiyama | H02N 11/00 |
| | | | 310/300 |
| 2013/0319118 A1* | 12/2013 | Deng | G01P 15/125 |
| | | | 427/79 |
| 2014/0010052 A1* | 1/2014 | Torashima | B06B 1/0292 |
| | | | 367/181 |
| 2014/0295606 A1* | 10/2014 | Larrey | G01D 5/02 |
| | | | 438/50 |
| 2015/0109880 A1* | 4/2015 | Kim | G01S 7/52017 |
| | | | 367/7 |
| 2015/0112181 A1* | 4/2015 | Yoon | A61B 8/5246 |
| | | | 600/407 |
| 2018/0130795 A1* | 5/2018 | Rothberg | A61B 8/4494 |
| 2019/0030569 A1 | 1/2019 | Najar et al. | |

OTHER PUBLICATIONS

Hung-Yu Chen et al., "A Low Impedance CMOS-MEMS Capacitive Resonator Based on Metal-Insulator-Metal (MIM) Capacitor Structure", IEEE Electron Device Letters, published on May 17, 2021, vol. 42, Issue 7, pp. 1045-1048, published by Institute of Electrical and Electronics Engineers (IEEE), U.S.A.

Hung-Yu Chen et al., "5V-BIAS CMOS-MEMS Capacitive Resonator With RM <5KΩ Based on Metal-Insulator-Metal (MIM) Capacitor", the 35th IEEE International Conference on Micro Electro Mechanical Systems (IEEE MEMS 2022), dated on Jan. 9-13, 2022, Poster Presentation, Japan.

\* cited by examiner

CAPACITIVE ULTRASONIC TRANSDUCER DEVICE, MANUFACTURING METHOD THEREOF AND TRANSDUCER ARRAY

RELATED APPLICATIONS

This application claims priority to Taiwan Application Serial Number 111136868, filed Sep. 28, 2022, which is herein incorporated by reference.

BACKGROUND

Technical Field

The present disclosure relates to a transducer device, a manufacturing method thereof and a transducer array. More particularly, the present disclosure relates to a capacitive ultrasonic transducer device, a manufacturing method thereof and a transducer array.

Description of Related Art

The conventional capacitive micromachined ultrasonic transducer (CMUT) integrates the micro-electromechanical devices of the CMUT with the circuit by wafer bonding or packaging. Due to a driving circuit of the capacitive transducer need to be driven by a high voltage, the development cost of the CMUT developed by System on a Chip (SoC) is higher, thereby increasing the cost of the micro-electromechanical system (MEMS) with large area.

Thus, a capacitive ultrasonic transducer device, which manufactures the micro-electromechanical capacitive ultrasonic elements on a Complementary Metal Oxide Semiconductor (CMOS) by a lost cost process, is commercially desirable.

SUMMARY

According to one aspect of the present disclosure, a capacitive ultrasonic transducer device includes a substrate, a first capacitive structure, a second capacitive structure, a first film structure and a second film structure. The first capacitive structure is disposed on the substrate, and includes a first electrode and a second electrode. A first gap and a dielectric layer are located between the first electrode and the second electrode. The second capacitive structure is disposed on the substrate, and includes a third electrode and a fourth electrode. A second gap is located between the third electrode and the fourth electrode. The first film structure is connected to the first electrode and the dielectric layer, and configured to seal the first gap. The second film structure is connected to the third electrode and the fourth electrode, and configured to seal the second gap. A first width between the first electrode and the second electrode is different from a second width of the second gap.

According to another aspect of the present disclosure, a transducer array includes a plurality of capacitive ultrasonic transducer devices and an interface circuit. At least one of the capacitive ultrasonic transducer devices includes a substrate, a first capacitive structure, a second capacitive structure, a first film structure and a second film structure. The first capacitive structure is disposed on the substrate, and includes a first electrode and a second electrode. A first gap and a dielectric layer are located between the first electrode and the second electrode. The second capacitive structure is disposed on the substrate, and includes a third electrode and a fourth electrode. A second gap is located between the third electrode and the fourth electrode. The first film structure is connected to the first electrode and the dielectric layer, and configured to seal the first gap. The second film structure is connected to the third electrode and the fourth electrode, and configured to seal the second gap. The interface circuit is for the capacitive ultrasonic transducer devices stacking thereon, and electrically connected to the capacitive ultrasonic transducer devices. A first width between the first electrode and the second electrode is different from a second width of the second gap.

According to further another aspect of the present disclosure, a manufacturing method of a capacitive ultrasonic transducer device includes performing a printing step, a first etching step, a second etching step, a third etching step and a film disposing step. The printing step is performed to print a first capacitive precursor structure and a second capacitive precursor structure on a substrate. The first etching step is performed to etch a metallic compound of the first capacitive precursor structure and a metallic compound of the second capacitive precursor structure to form a plurality of openings according to an isotropic wet etching process. The second etching step is performed to etch a dielectric layer of the first capacitive precursor structure and a dielectric layer of the second capacitive precursor structure from the openings according to an anisotropy dry etching process. The third etching step is performed to etch an aluminum copper alloy of the first capacitive precursor structure and an aluminum copper alloy of the second capacitive precursor structure to form a first capacitive structure and a second capacitive structure, respectively, according to the isotropic wet etching process. The film disposing step is performed to dispose a first film structure and a second film structure on a surface of the first capacitive structure and a surface of the second capacitive structure, respectively.

BRIEF DESCRIPTION OF THE DRAWINGS

The present disclosure can be more fully understood by reading the following detailed description of the embodiment, with reference made to the accompanying drawings as follows.

DETAILED DESCRIPTION

The embodiment will be described with the drawings. For clarity, some practical details will be described below. However, it should be noted that the present disclosure should not be limited by the practical details, that is, in some embodiment, the practical details is unnecessary. In addition, for simplifying the drawings, some conventional structures and elements will be simply illustrated, and repeated elements may be represented by the same labels.

It will be understood that when an element (or device) is referred to as be "connected to" another element, it can be directly connected to other element, or it can be indirectly connected to the other element, that is, intervening elements may be present. In contrast, when an element is referred to as be "directly connected to" another element, there are no intervening elements present. In addition, the terms first, second, third, etc. are used herein to describe various elements or components, these elements or components should not be limited by these terms. Consequently, a first element or component discussed below could be termed a second element or component.

Figure 1:
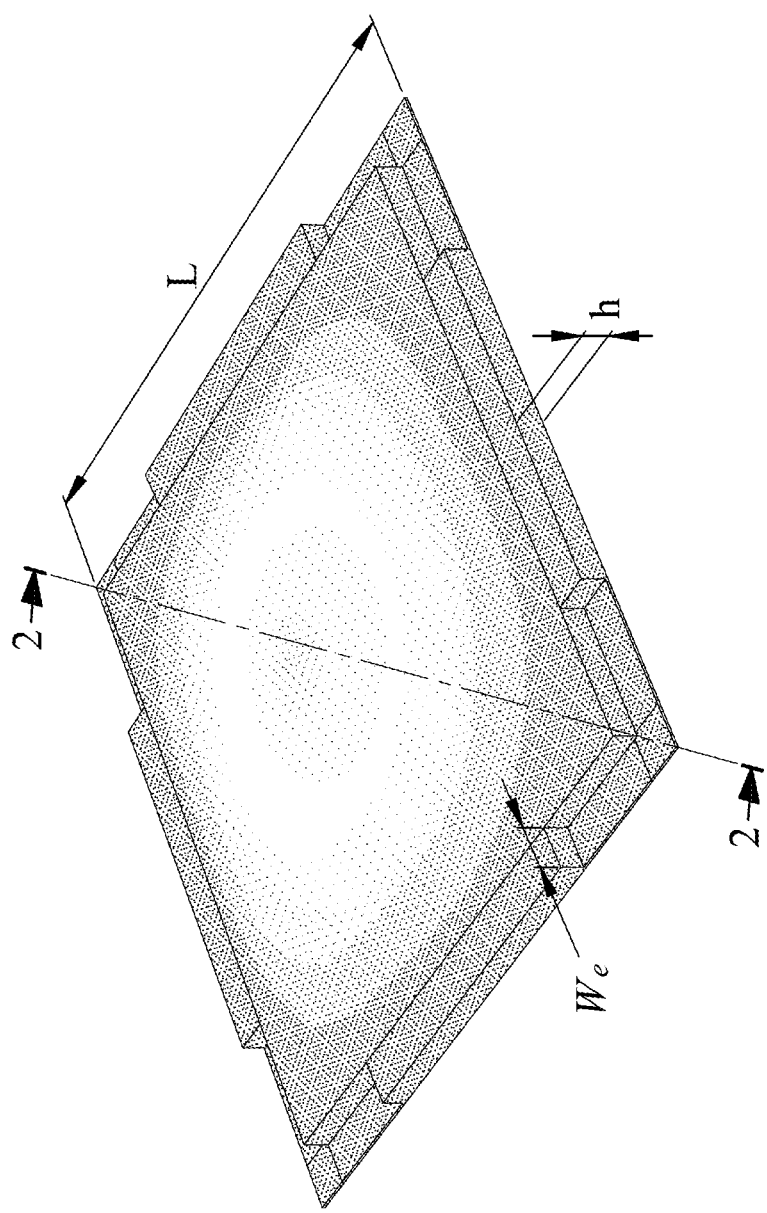
FIG. 1 shows a schematic view of a capacitive ultrasonic transducer device according to a first embodiment of the present disclosure.
Figure 2:
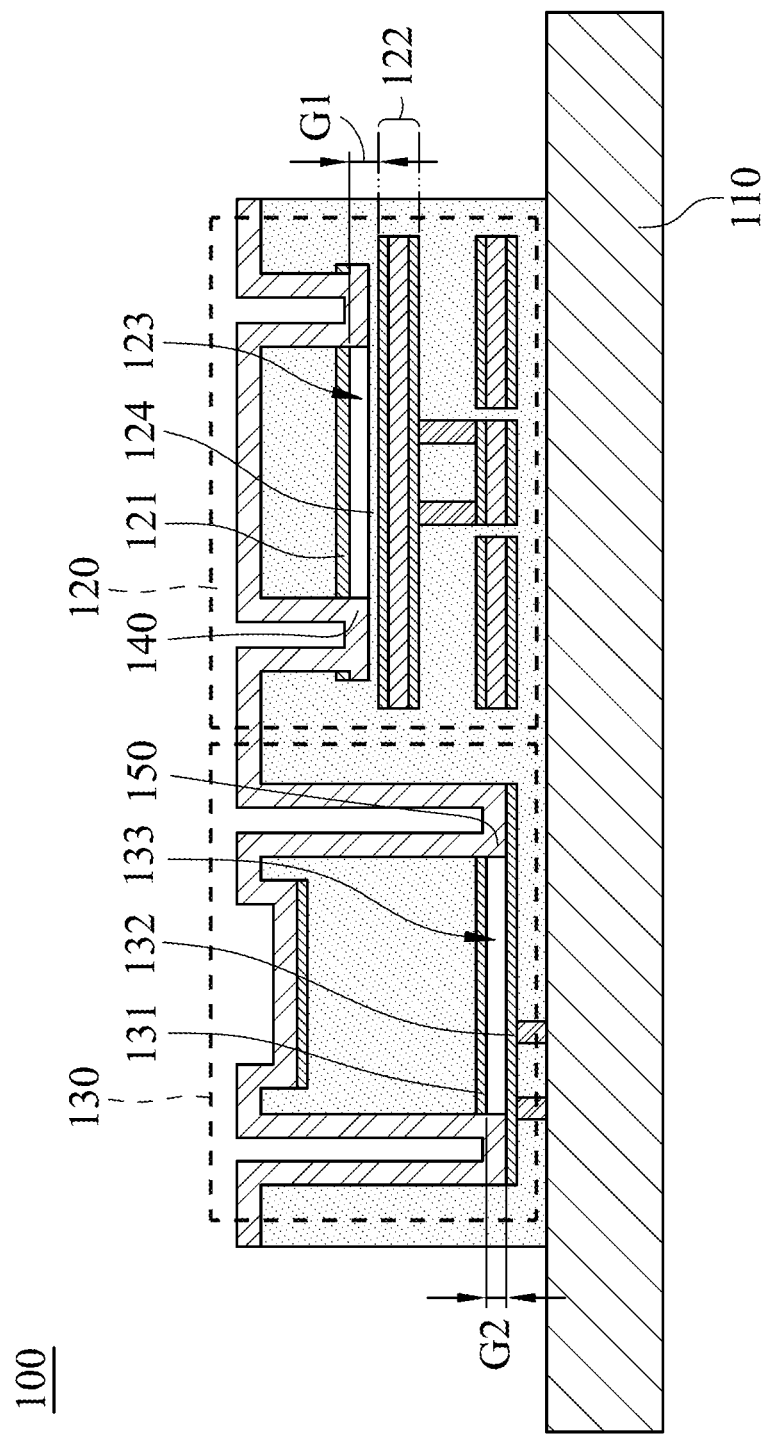
FIG. 2 shows a cross-sectional view of the capacitive ultrasonic transducer device along line 2-2 of FIG. 1.

Please refer to FIG. 1 and FIG. 2. FIG. 1 shows a schematic view of a capacitive ultrasonic transducer device 100 according to a first embodiment of the present disclosure. FIG. 2 shows a cross-sectional view of the capacitive ultrasonic transducer device 100 along line 2-2 of FIG. 1. The capacitive ultrasonic transducer device 100 includes a substrate 110, a first capacitive structure 120, a second capacitive structure 130, a first film structure 140 and a second film structure 150. The first capacitive structure 120 is disposed on the substrate 110, and includes a first electrode 121 and a second electrode 122. A first gap 123 and a dielectric layer 124 are located between the first electrode 121 and the second electrode 122. The second capacitive structure 130 is disposed on the substrate 110, and includes a third electrode 131 and a fourth electrode 132. A second gap 133 is located between the third electrode 131 and the fourth electrode 132. The first film structure 140 is connected to the first electrode 121 and the dielectric layer 124, and configured to seal the first gap 123. The second film structure 150 is connected to the third electrode 131 and the fourth electrode 132, and configured to seal the second gap 133. A first width G1 between the first electrode 121 and the second electrode 122 is different from a second width G2 of the second gap 133. Thus, the capacitive ultrasonic transducer device 100 of the present disclosure can provide different capacitive transduction gaps with different widths (i.e., the first width G1 and the second width G2) so as to increase the application flexibility of a capacitive ultrasonic element.

Moreover, the substrate 110 can be a metal connecting layer of a Complementary Metal Oxide Semiconductor (CMOS). The first capacitive structure 120 can be a Metal-Inductor-Metal (MIM) structure. The second capacitive structure 130 can be a Titanium Nitride (TiN) capacitive structure. Each of the first electrode 121, the third electrode 131 and the fourth electrode 132 can be TiN. The second electrode 122 can be a metal layer of a sandwich structure. The dielectric layer 124 can be located on the second electrode 122, and a thickness of the dielectric layer 124 can be 40 nanometer (nm). Each of the first film structure 140 and the second film structure 150 can be a dielectric material or film formed by a thin film deposition process. The first film structure 140 is connected from each of the two ends of the first electrode 121 to the dielectric layer 124, thereby sealing the first gap 123. The second film structure 150 is connected from each of the two ends of the third electrode 131 to the fourth electrode 132, thereby sealing the second gap 133. Thus, the capacitive ultrasonic transducer device 100 of the present disclosure has different capacitive structures (i.e., the MIM structure and the TiN capacitive structure) at the same time.

In the first embodiment, the substrate 110 can be a metal connecting layer on a 0.18 micrometer (μm) CMOS platform, the first capacitive structure 120 can be a Capacitor-Top-Metal (CTM) between a M5 metal layer and a M6 metal layer, the first electrode 121 can be TiN of the aforementioned CTM, the second electrode 122 can be the M5 metal layer, the second capacitive structure 130 can be a M4 metal layer, the third electrode 131 and the fourth electrode 132 can be two TiN layers of the M4 metal layer, but the present disclosure is not limited thereto. Moreover, the capacitive ultrasonic transducer device 100 of the present disclosure utilizes the structure over the M4 metal layer to form the first capacitive structure 120 and the second capacitive structure 130, and reserves the structure under the M4 metal layer to increase the programming flexibility of the circuit.

In detail, by sealing the first capacitive structure 120 and the second capacitive structure 130 via the first film structure 140 and the second film structure 150, respectively, the capacitive ultrasonic transducer device 100 can be applied to one of a solid-state environment and a liquid environment. In the first embodiment, the capacitive ultrasonic transducer device 100 can be a fingerprint sensing device, a mass sensing device disposed under water or disposed in the electrolytic solution, but the present disclosure is not limited thereto. Moreover, by sealing the first gap 123 and the second gap 133 via the first film structure 140 and the second film structure 150, respectively, the first gap 123 and the second gap 133 are under a vacuum state. In the vacuum state, the pressure is relatively low, the air damping can be decreased, and the Q factor can be increased. Therefore, the capacitive ultrasonic transducer device 100 of the present disclosure can have sufficient electromechanical conversion performance while disposing in normal atmosphere environment and the liquid environment.

Furthermore, the first capacitive structure 120 can be a receiver, and the second capacitive structure 130 can be a transmitter. The first width G1 is less than the second width G2. The first width G1 is greater than or equal to 100 nm, and less than or equal to 150 nm. The second width G2 is greater than or equal to 350 nm, and less than or equal to 450 nm. In the first embodiment, the first width G1 can be 120 nm, the second width G2 can be 450 nm, but the present disclosure is not limited thereto. Because the first width G1 of the first capacitive structure 120 is narrow, the first capacitive structure 120 can provide great electromechanical conversion efficiency, and the first capacitive structure 120 can also have great electromechanical transduction efficiency without driven by a high voltage. Moreover, the receiver (i.e., the first capacitive structure 120) has high sensitivity. The second width G2 of the second capacitive structure 130 is wider, and the film displacement generated by the second capacitive structure 130 is greater. Thus, the capacitive ultrasonic transducer device 100 of the present disclosure can have high detecting sensitivity and high displacement, and also can be driven by low voltage (under 25 V).

Please refer to FIG. 1, a thickness h of the first film structure 140 and a thickness h of the second film structure 150 of the capacitive ultrasonic transducer device 100 can be both greater than or equal to 0.5 µm, and less than or equal to 5 µm. The etching width W e can be greater than or equal to 5 µm, and less than or equal to 20 µm. In the first embodiment, a length L of the capacitive ultrasonic transducer device 100 can be greater than or equal to 30 µm, and less than or equal to 100 µm. The capacitive ultrasonic transducer device 100 can etch from an edge, which has a lower oscillation speed.

Figure 3:
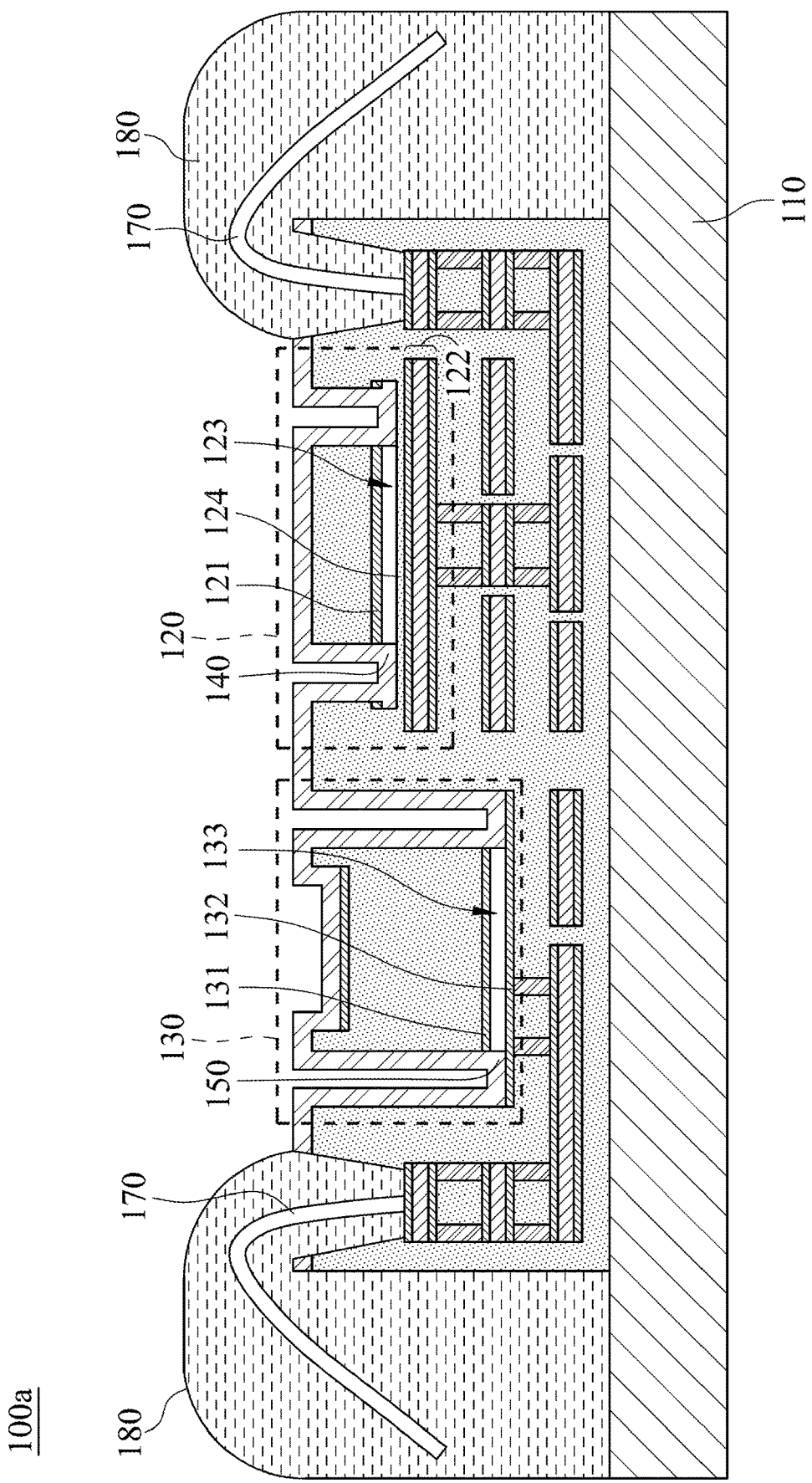
FIG. 3 shows a cross-sectional view of a capacitive ultrasonic transducer device according to a second embodiment of the present disclosure.

Please refer to FIG. 1 to FIG. 3. FIG. 3 shows a cross-sectional view of a capacitive ultrasonic transducer device 100a according to a second embodiment of the present disclosure. The capacitive ultrasonic transducer device 100a includes a substrate 110, a first capacitive structure 120, a second capacitive structure 130, a first film structure 140 and a second film structure 150. In the second embodiment, the substrate 110, a first capacitive structure 120, the second capacitive structure 130, the first film structure 140 and the second film structure 150 of the capacitive ultrasonic transducer device 100a are the same as the substrate 110, a first capacitive structure 120, the second capacitive structure 130, the first film structure 140 and the second film structure 150 of the capacitive ultrasonic transducer device 100, respectively, and will not be described again herein. The capacitive ultrasonic transducer device 100a can further include two conductive structures 170 and two isolation layers 180. The two conductive structures 170 are electrically connected to the first capacitive structure 120 and the second capacitive structure 130, respectively. The two isolation layers 180 cover the two conductive structures 170, respectively. Thus, the capacitive ultrasonic transducer device 100a can be disposed under water or in the electrolytic solution.

Figure 4:
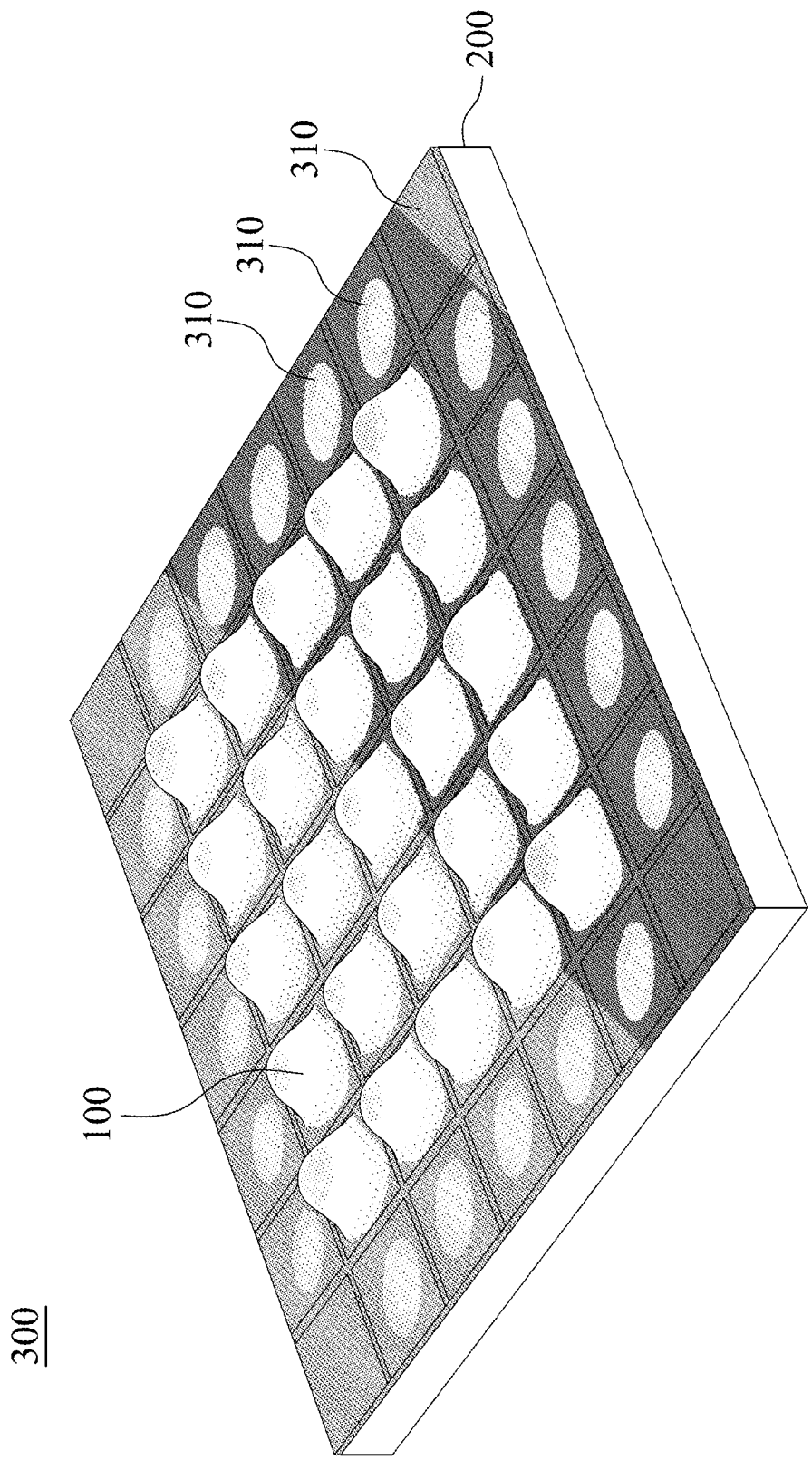
FIG. 4 shows a schematic view of a transducer array according to a third embodiment of the present disclosure.

Please refer to FIG. 2, FIG. 3 and FIG. 4. FIG. 4 shows a schematic view of a transducer array 300 according to a third embodiment of the present disclosure. The transducer array 300 includes a plurality of capacitive ultrasonic transducer devices 100 and an interface circuit 200. In the third embodiment, each of the capacitive ultrasonic transducer devices 100 can be the same as the capacitive ultrasonic transducer device 100 in the first embodiment or the capacitive ultrasonic transducer device 100a in the second embodiment, and will not be described again herein. The interface circuit 200 is for the capacitive ultrasonic transducer devices 100 stacking thereon, and electrically connected to the capacitive ultrasonic transducer devices 100. Thus, the area and the wiring complexity of the transducer array 300 can be reduced by manufacturing the capacitive ultrasonic transducer devices 100 on the CMOS, and disposing the interface circuit 200 under the capacitive ultrasonic transducer devices 100 vertically.

Moreover, due to the boundary condition of the peripheral section 310 of the transducer array 300 is different from the capacitive ultrasonic transducer devices 100, the natural frequency of the peripheral section 310 is different from the natural frequency of the capacitive ultrasonic transducer devices 100. Therefore, the capacitive ultrasonic transducer devices 100 are not disposed on the peripheral section 310 of the transducer array 300.

Figure 5:
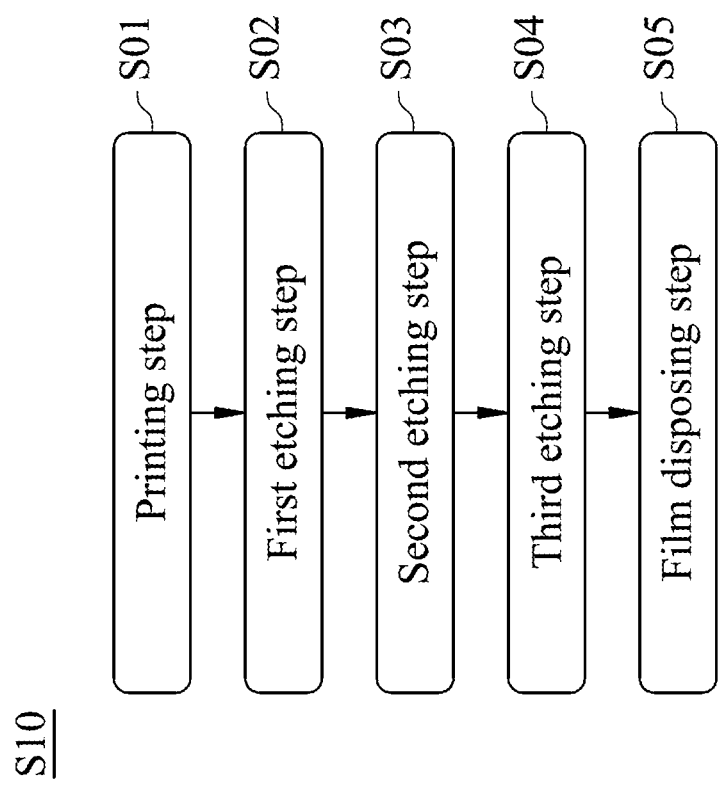
FIG. 5 shows a flow chart of a manufacturing method of a capacitive ultrasonic transducer device according to a fourth embodiment of the present disclosure.
Figure 6:
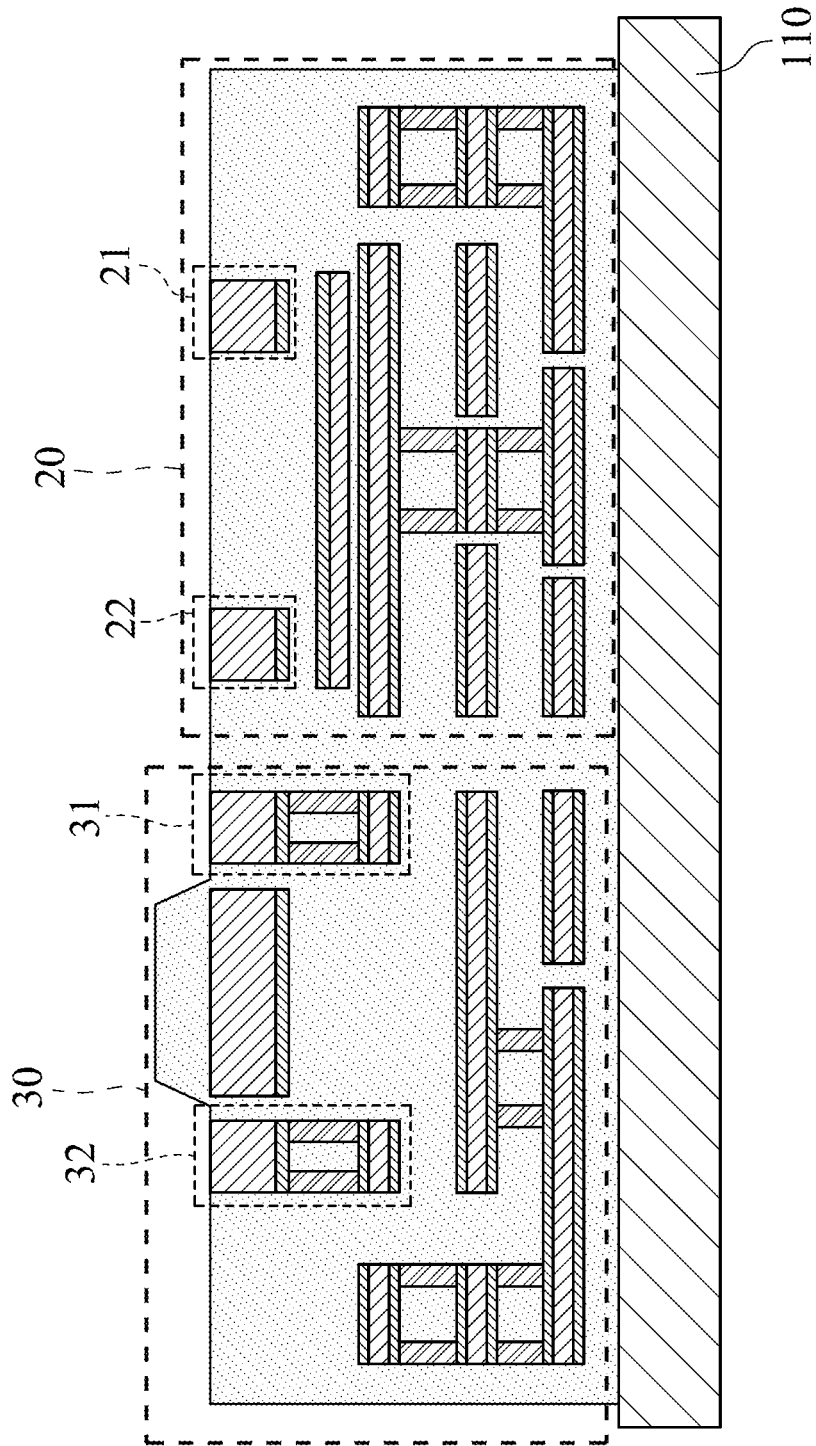
FIG. 6 shows a schematic view of a printing step of the manufacturing method of the capacitive ultrasonic transducer device according to the embodiment in FIG. 5.
Figure 7:
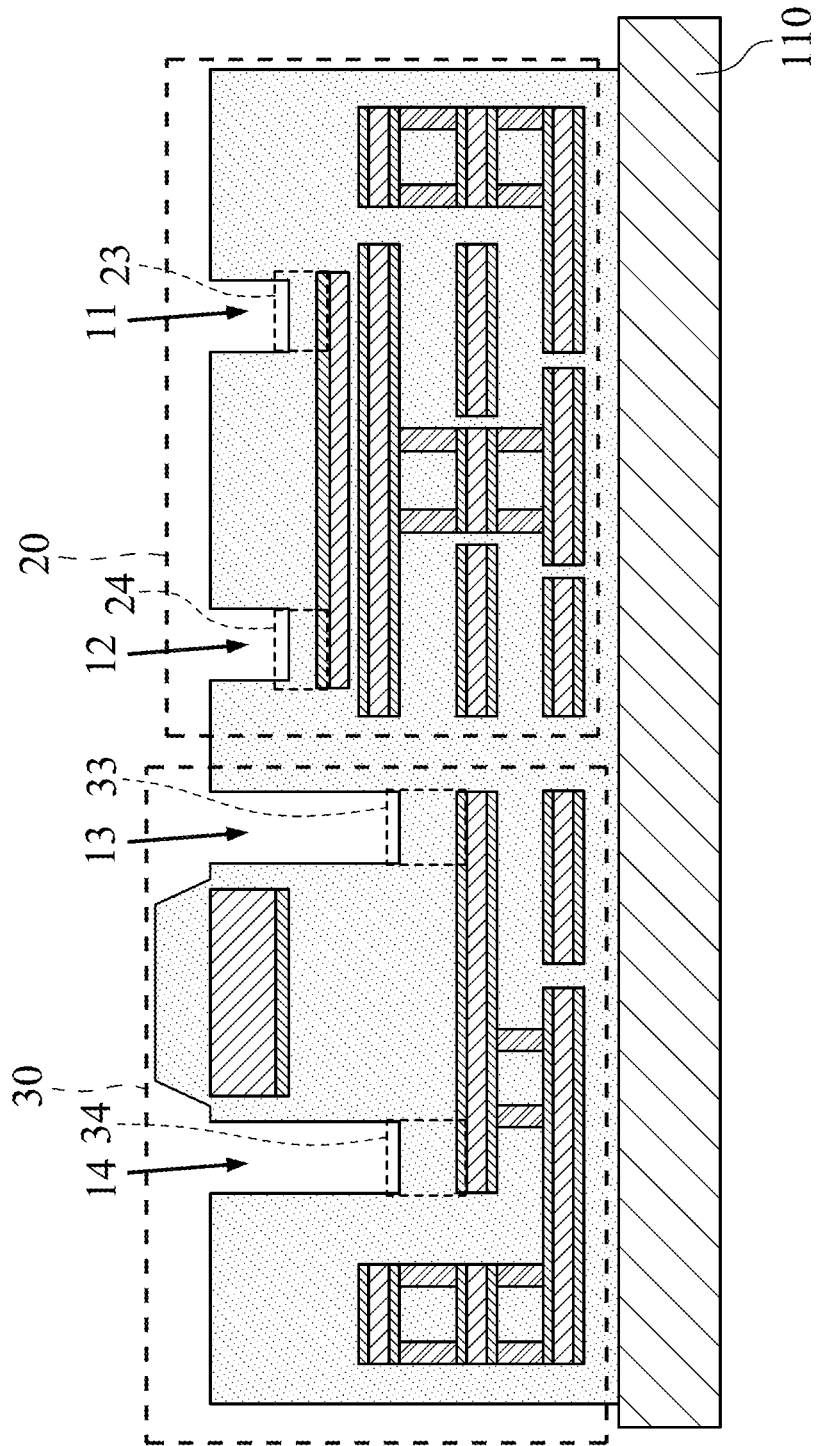
FIG. 7 shows a schematic view of a first etching step of the manufacturing method of the capacitive ultrasonic transducer device according to the embodiment in FIG. 5.
Figure 8:
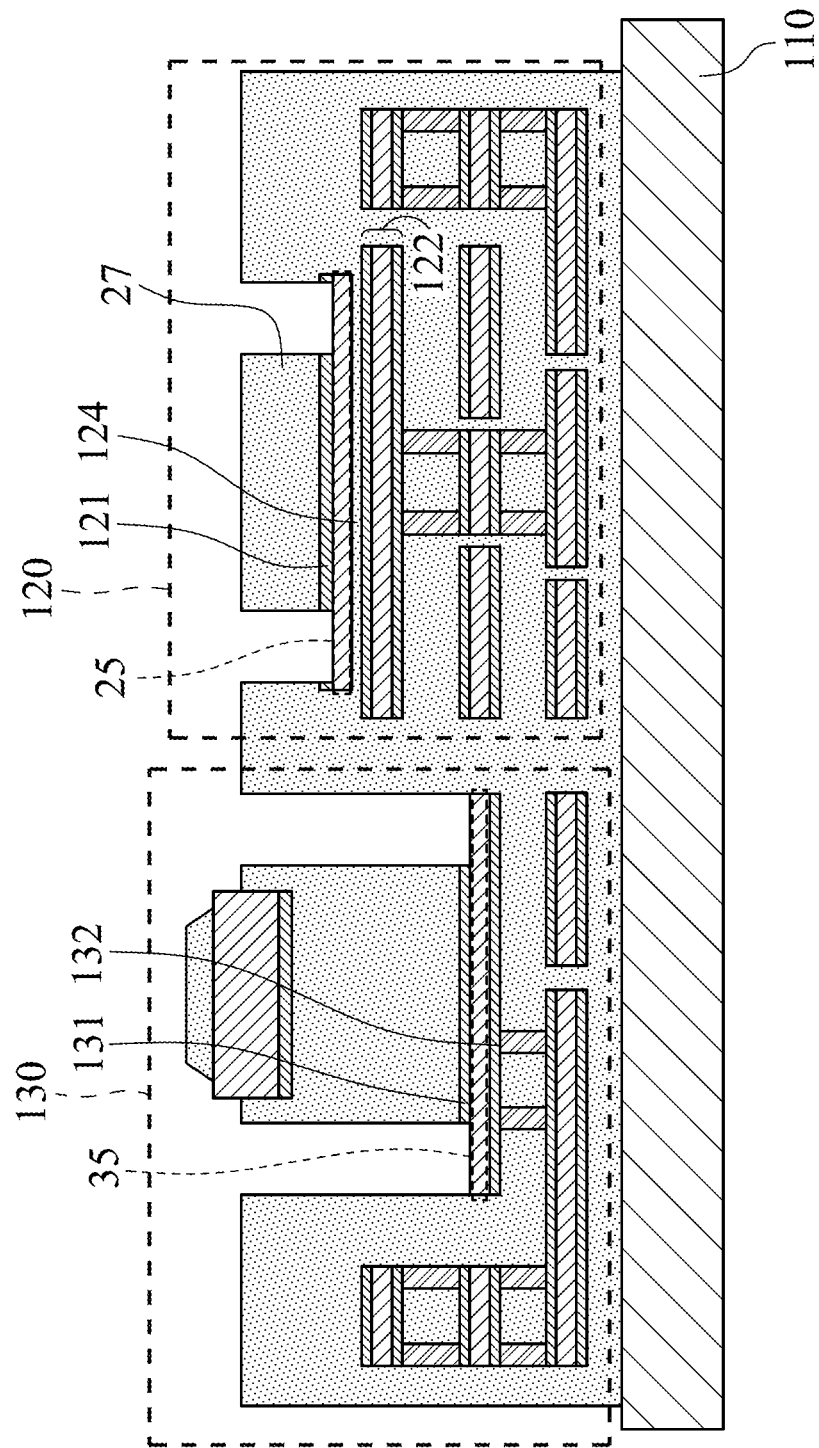
FIG. 8 shows a schematic view of a second etching step of the manufacturing method of the capacitive ultrasonic transducer device according to the embodiment in FIG. 5.
Figure 9:
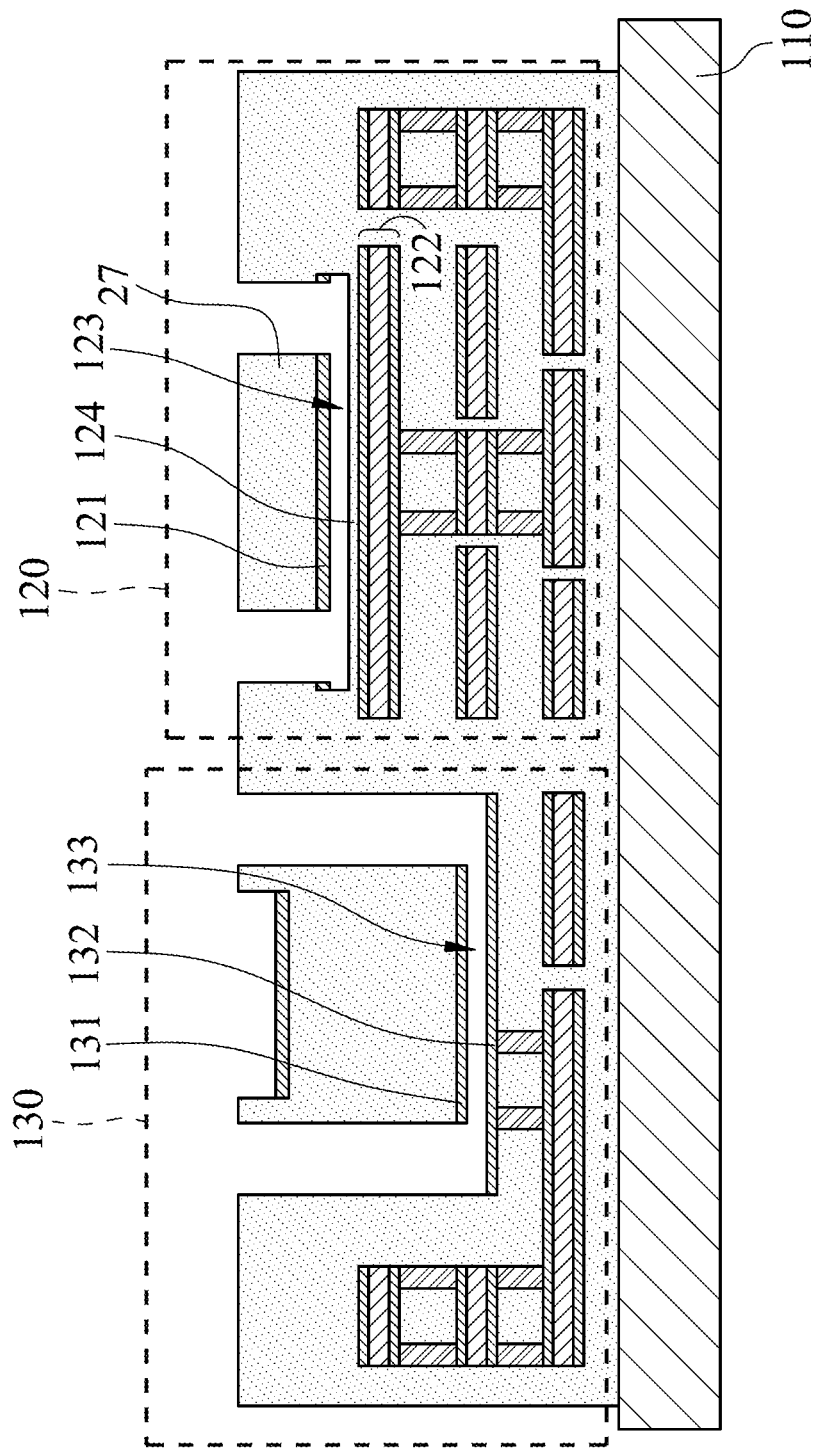
FIG. 9 shows a schematic view of a third etching step of the manufacturing method of the capacitive ultrasonic transducer device according to the embodiment in FIG. 5.
Figure 10:
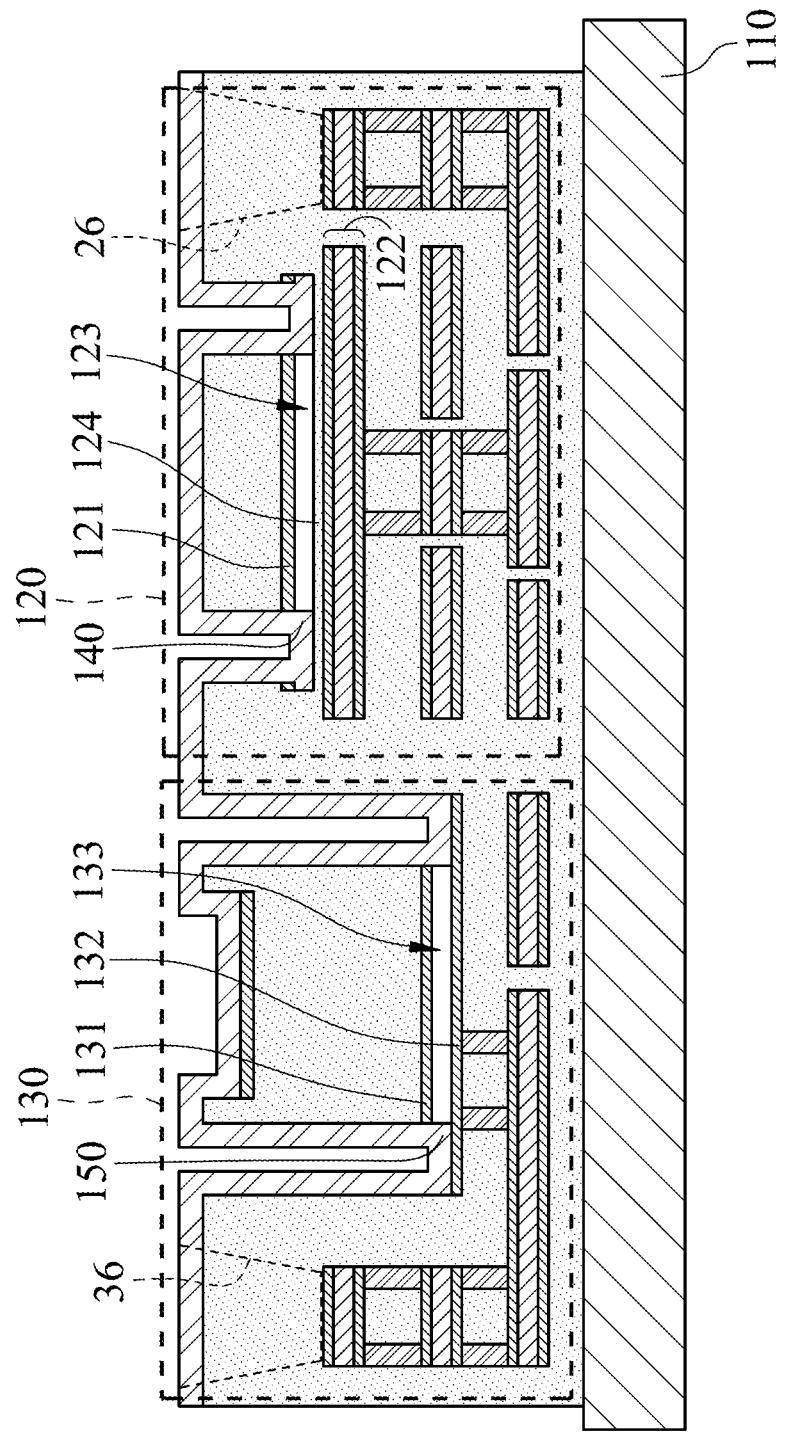
FIG. 10 shows a schematic view of a film disposing step of the manufacturing method of the capacitive ultrasonic transducer device according to the embodiment in FIG. 5.

Please refer to FIG. 2 and FIG. 5 to FIG. 10. FIG. 5 shows a flow chart of a manufacturing method S10 of a capacitive ultrasonic transducer device 100 according to a fourth embodiment of the present disclosure. FIG. 6 shows a schematic view of a printing step S01 of the manufacturing method S10 of the capacitive ultrasonic transducer device 100 according to the embodiment in FIG. 5. FIG. 7 shows a schematic view of a first etching step S02 of the manufacturing method S10 of the capacitive ultrasonic transducer device 100 according to the embodiment in FIG. 5. FIG. 8 shows a schematic view of a second etching step S03 of the manufacturing method S10 of the capacitive ultrasonic transducer device 100 according to the embodiment in FIG. 5. FIG. 9 shows a schematic view of a third etching step S04 of the manufacturing method S10 of the capacitive ultrasonic transducer device 100 according to the embodiment in FIG. 5. FIG. 10 shows a schematic view of a film disposing step S05 of the manufacturing method S10 of the capacitive ultrasonic transducer device according to the embodiment in FIG. 5. The manufacturing method S10 of the capacitive ultrasonic transducer device 100 includes performing the printing step S01, the first etching step S02, the second etching step S03, the third etching step S04 and the film disposing step S05.

In the printing step S01, a first capacitive precursor structure 20 and a second capacitive precursor structure 30 are printed on a substrate 110.

In the first etching step S02, the metallic compounds 21, 22 of the first capacitive precursor structure 20 and the metallic compounds 31, 32 of the second capacitive precursor structure 30 are etched to form a plurality of openings 11, 12, 13, 14 according to an isotropic wet etching process. In detail, the isotropic wet etching process etches the metallic compounds 21, 22, 31, 32 via an etching solution with $H_2SO_4$ and $H_2O_2$, but the present disclosure is not limited thereto.

In the second etching step S03, the dielectric layers 23, 24 of the first capacitive precursor structure 20 and the dielectric layers 33, 34 of the second capacitive precursor structure 30 are etched from the openings 11, 12, 13, 14 according to an anisotropy dry etching process. In detail, the anisotropy dry etching process can be a Reactive Ion Etching (RIE), but the present disclosure is not limited thereto.

In the third etching step S04, an aluminum copper alloy 25 of the first capacitive precursor structure 20 and an aluminum copper alloy 35 of the second capacitive precursor structure 30 are etched to form a first capacitive structure 120 (as shown in FIG. 9) and a second capacitive structure 130 (as shown in FIG. 9), respectively, according to the isotropic wet etching process.

In the film disposing step S05, a first film structure 140 and a second film structure 150 are disposed on a surface of the first capacitive structure 120 and a surface of the second capacitive structure 130, respectively to form the capacitive ultrasonic transducer device 100 in FIG. 2. In the fourth embodiment, the capacitive ultrasonic transducer device 100 can be the same as the capacitive ultrasonic transducer device 100 in the first embodiment, and the present disclosure is not limited thereto.

Thus, the manufacturing method S10 of the capacitive ultrasonic transducer device 100 can manufacture the first capacitive structure 120 and the second capacitive structure 130 of the capacitive ultrasonic transducer device 100 on the CMOS at the same time by same manufacturing process (i.e., the isotropic wet etching process and the anisotropy dry etching process) with low cost, thereby decreasing the manufacturing cost of the capacitive ultrasonic system.

Figure 11:
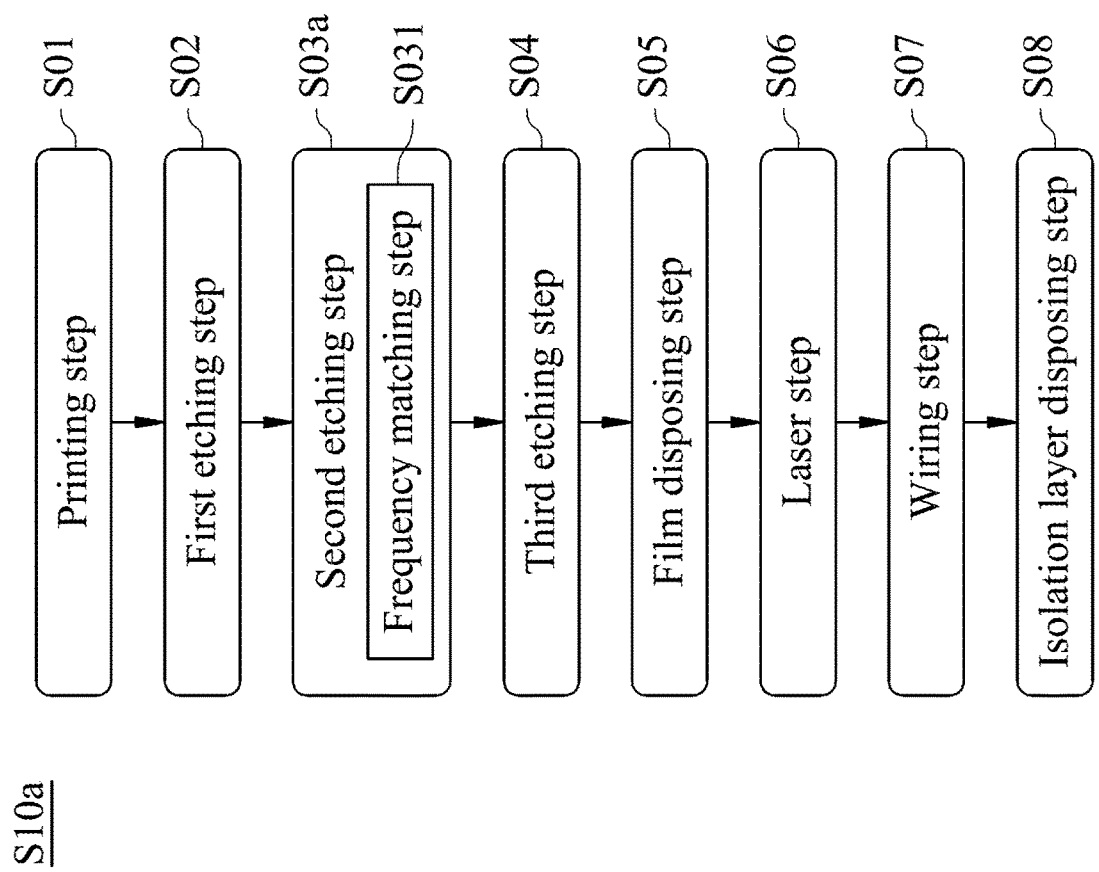
FIG. 11 shows a flow chart of a manufacturing method of a capacitive ultrasonic transducer device according to a fifth embodiment of the present disclosure.
Figure 12:
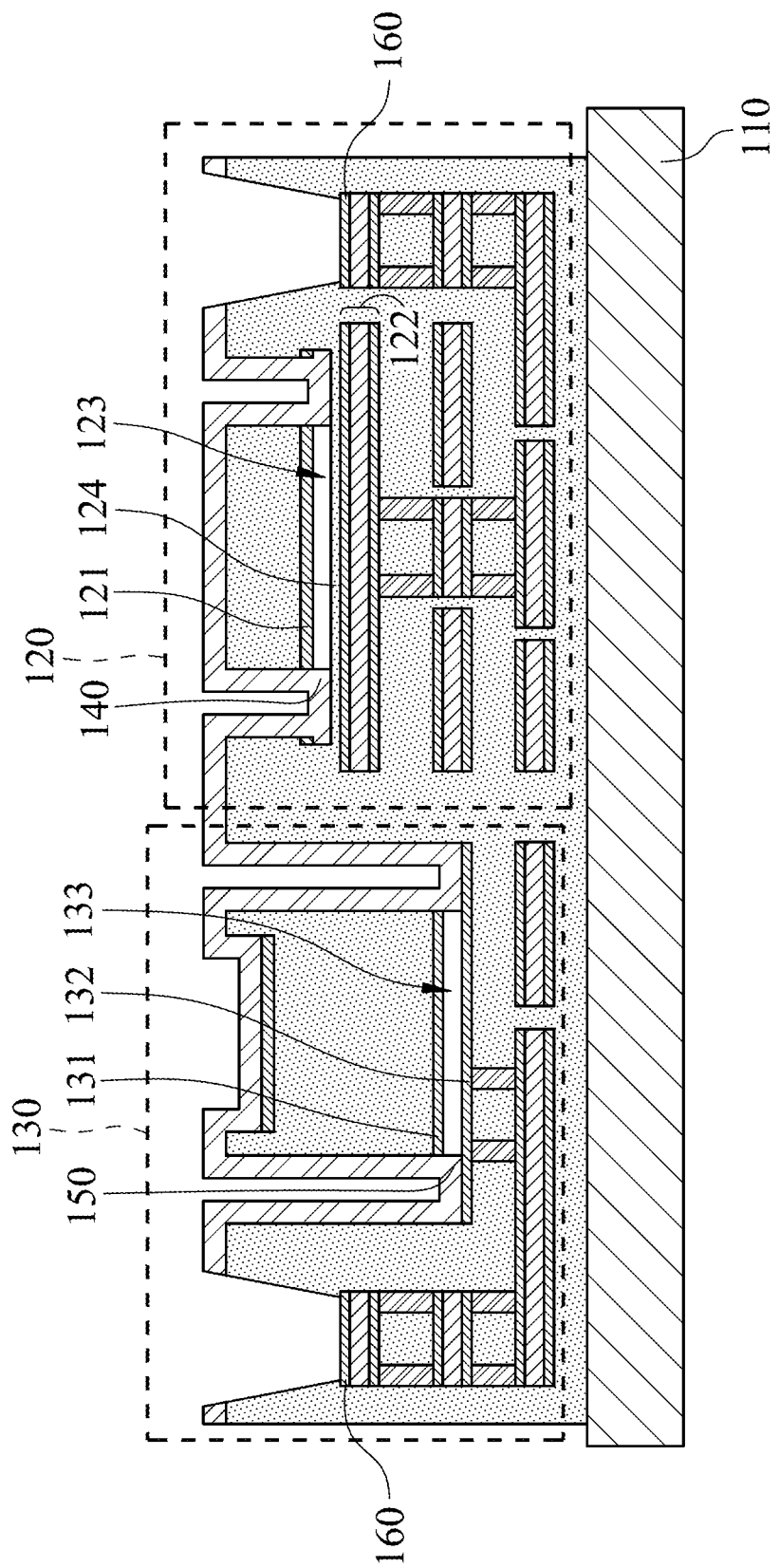
FIG. 12 shows a schematic view of a laser step of the manufacturing method of the capacitive ultrasonic transducer device according to the embodiment in FIG. 11.
Figure 13:
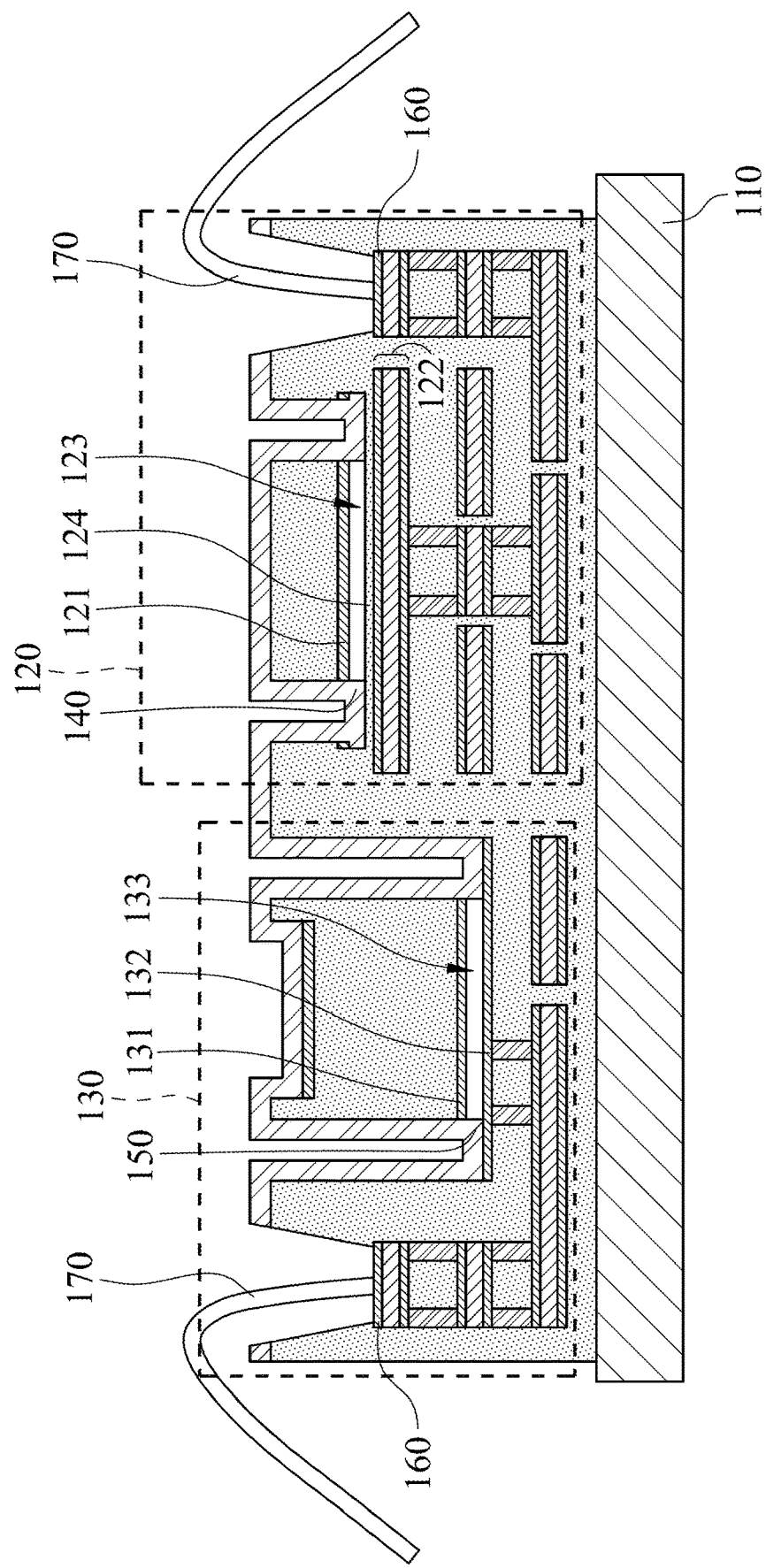
FIG. 13 shows a schematic view of a wiring step of the manufacturing method of the capacitive ultrasonic transducer device according to the embodiment in FIG. 11.

Please refer to FIG. 1, FIG. 3, FIG. 5 and FIG. 11 to FIG. 13. FIG. 11 shows a flow chart of a manufacturing method S10a of a capacitive ultrasonic transducer device 100a according to a fifth embodiment of the present disclosure. FIG. 12 shows a schematic view of a laser step S06 of the manufacturing method S10a of the capacitive ultrasonic transducer device 100a according to the embodiment in FIG. 11. FIG. 13 shows a schematic view of a wiring step S07 of the manufacturing method S10a of the capacitive ultrasonic transducer device 100a according to the embodiment in FIG. 11. The manufacturing method S10a of the capacitive ultrasonic transducer device 100a includes performing a printing step S01, a first etching step S02, a second etching step S03a, a third etching step S04, a film disposing step S05, the laser step S06, the wiring step S07 and an isolation layer disposing step S08. In the fifth embodiment, the printing step S01, the first etching step S02, the third etching step S04 and the film disposing step S05 are the same as the printing step S01, the first etching step S02, the third etching step S04 and the film disposing step S05 in the fourth embodiment, respectively, and will not be described again herein. The manufacturing method S10a of the capacitive ultrasonic transducer device 100a can further include the laser step S06, the wiring step S07 and the isolation layer disposing step S08. The second etching step S03a can include a frequency matching step S031.

In the frequency matching step S031, a resonance frequency of the first capacitive structure 120 and a resonance frequency of the second capacitive structure 130 are adjusted according to an etching time of the second etching step S03a. Moreover, the frequency matching step S031 can adjust a thickness of the dielectric layer 27 (as shown in FIG. 8 and FIG. 9) to match a natural frequency of the first capacitive structure 120 and a natural frequency of the second capacitive structure 130 by extending or shortening the etching time of the second etching step S03a.

In other embodiment, the manufacturing method of the capacitive ultrasonic transducer device can adjust a bias applied on one of the first capacitive structure and the second capacitive structure to match a natural frequency of the first capacitive structure and a natural frequency of the second capacitive structure according to an electrical soft spring effect. Because the first width of the first capacitive structure is narrower than the second width of the second capacitive structure, the first capacitive structure provides wider frequency adjusting range.

In the laser step S06, a partial dielectric layer 26 (as shown in FIG. 10) of the first capacitive structure 120 and a partial dielectric layer 36 (as shown in FIG. 10) of the second capacitive structure 130 are removed to form two conductive layers 160 according to a laser process.

In the wiring step S07, two conductive structures 170 are disposed on the two conductive layers 160 of the first capacitive structure 120 and the second capacitive structure 130, respectively. The two conductive structures 170 are electrically connected to the first capacitive structure 120 and the second capacitive structure 130, respectively.

In the isolation layer disposing step S08, the two conductive structures 170 are covered by two isolation layers 180, respectively, and the capacitive ultrasonic transducer device 100a (as shown in FIG. 3) is formed. In the fifth embodiment, the capacitive ultrasonic transducer device 100a can be the same as the capacitive ultrasonic transducer device 100a in the second embodiment, but the present disclosure is not limited thereto.

According to the aforementioned embodiments and examples, the advantages of the present disclosure are described as follows.

1. The capacitive ultrasonic transducer device of the present disclosure can provide different capacitive transduction gaps with different widths (i.e., the first width and the second width) so as to increase the application flexibility of a capacitive ultrasonic element.
2. The area and the wiring complexity of the transducer array can be reduced by manufacturing the capacitive ultrasonic transducer devices 100 on the CMOS, and disposing the interface circuit under the capacitive ultrasonic transducer devices vertically.
3. The manufacturing method of the capacitive ultrasonic transducer device can manufacture the first capacitive structure and the second capacitive structure of the capacitive ultrasonic transducer device on the CMOS at the same time by same manufacturing process (i.e., the isotropic wet etching process and the anisotropy dry etching process) with low cost, thereby decreasing the manufacturing cost of the capacitive ultrasonic system.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A capacitive ultrasonic transducer device, comprising:
   a substrate;
   a first capacitive structure disposed on the substrate, and comprising:
      a first electrode; and
      a second electrode, a first gap and a dielectric layer located between the first electrode and the second electrode;
   a second capacitive structure disposed on the substrate, and comprising:
      a third electrode; and
      a fourth electrode, a second gap located between the third electrode and the fourth electrode;
   a first film structure connected to the first electrode and the dielectric layer, and configured to seal the first gap; and
   a second film structure connected to the third electrode and the fourth electrode, and configured to seal the second gap;
   wherein a first width between the first electrode and the second electrode is different from a second width of the second gap.

2. The capacitive ultrasonic transducer device of claim 1, wherein the first capacitive structure is a receiver, the second capacitive structure is a transmitter, and the first width is less than the second width.

3. The capacitive ultrasonic transducer device of claim 1, wherein the first width is greater than or equal to 100 nanometer (nm), and less than or equal to 150 nm, and the second width is greater than or equal to 350 nm, and less than or equal to 450 nm.

4. The capacitive ultrasonic transducer device of claim 1, wherein the first capacitive structure is a metal-inductor-metal (MIM) structure, and the second capacitive structure is a titanium nitride (TiN) capacitive structure.

5. The capacitive ultrasonic transducer device of claim 1, wherein the capacitive ultrasonic transducer device is applied to one of a solid-state environment and a liquid environment.

6. The capacitive ultrasonic transducer device of claim 1, wherein a thickness of the first film structure and a thickness of the second film structure are both greater than or equal to 0.5 micrometer ($\mu$m) and less than or equal to 5 $\mu$m.

7. The capacitive ultrasonic transducer device of claim 1, further comprising:
  two conductive structures electrically connected to the first capacitive structure and the second capacitive structure, respectively; and
  two isolation layers covering the two conductive structures, respectively.

8. A transducer array, comprising:
a plurality of capacitive ultrasonic transducer devices, at least one of the capacitive ultrasonic transducer devices comprising:
  a substrate;
  a first capacitive structure disposed on the substrate, and comprising:
    a first electrode; and
    a second electrode, a first gap and a dielectric layer located between the first electrode and the second electrode;
  a second capacitive structure disposed on the substrate, and comprising:
    a third electrode; and
    a fourth electrode, a second gap located between the third electrode and the fourth electrode;
  a first film structure connected to the first electrode and the dielectric layer, and configured to seal the first gap; and
  a second film structure connected to the third electrode and the fourth electrode, and configured to seal the second gap; and
an interface circuit for the capacitive ultrasonic transducer devices stacking thereon, and electrically connected to the capacitive ultrasonic transducer devices;
wherein a first width between the first electrode and the second electrode is different from a second width of the second gap.

* * * * *